United States Patent [19]
Kitchell et al.

[11] Patent Number: 5,262,313
[45] Date of Patent: Nov. 16, 1993

[54] CARRAGEEMAN-IMMOBILIZED ESTERASE

[75] Inventors: Barbara S. Kitchell, Austin, Tex.; Robert W. Henkens, Durham, N.C.; Philip Brown, Durham, N.C.; Steven W. Baldwin, Durham, N.C.; Charles H. Lochmüller, Durham, N.C.; John P. O'Daly, Carrboro, N.C.

[73] Assignee: Andcare, Inc., Durham, N.C.

[21] Appl. No.: 715,829

[22] Filed: Jun. 14, 1991

[51] Int. Cl.$^5$ .......................... C12P 7/62; C12P 7/64; C12N 11/10; C12N 9/20
[52] U.S. Cl. ................................. 435/135; 435/134; 435/178; 435/182; 435/198
[58] Field of Search ............... 435/134, 135, 174, 177, 435/178, 180, 198

[56] References Cited

U.S. PATENT DOCUMENTS

| | | | |
|---|---|---|---|
| 4,138,292 | 2/1979 | Chibata et al. | 435/178 |
| 4,433,054 | 2/1984 | Chitaba et al. | 435/178 |
| 4,800,162 | 1/1989 | Matson | 435/280 |
| 5,108,916 | 4/1992 | Cobbs et al. | 435/198 X |

OTHER PUBLICATIONS

Fadnavis, N. et al. (1989), "Immobilized Enzymes in Reverse Micelles: Studies with Gel-entrapped Trypsin and α-Chymotrypsin in AOT Reverse Micelles," *Biotechnology and Bioengineering*, 33:1277-1282.

Fujisawa, T., and Toshio, S. (1987), "Reduction of Carboxylic Acids to Aldehydes: 6-Oxodecanal," *Org. Syn.*, 66:121-126.

Hashimoto, S., et al. (1986), "A Novel Lithium Iodide-Promoted Vinylcyclopropane-Cyclopentene Rearrangement: Efficient Synthesis of Bicyclo[3.3.0]Oct-6-En-2-One, Versatile Building Block for Polycyclopentanoid Natural Products," *Tetrahedron Lett.*, 27(25):2885-2888.

Rosen, T., et al. (1984), "A Convenient Assay for the Optical Purity of Monomethyl 3-Hydroxypentanedioate," *J. Org. Chem.*, 49:3657-3659.

Inada, Y., et al. (1986), "Application of Polyethylene Glycol-Modified Enzymes in Biotechnological Processes: Organic Solvent-Soluble Enzymes," *TibTech*, 190-194.

Zaks, A. and Klibanov, A. (1985), "Enzyme-Catalyzed Processes in Organic Solvents," *Proc. Natl. Acad. Sci. U.S.A.*, 82:3192-3196.

Lochmüller, C. and Wigman, L. (1987), "Aerosol-Jet Produced, Magnetic Carrageenan-Gel Particles: A New Affinity Chromatography Matrix," *J. Chem Tech. Biotechnol.*, 40:33-40.

Luisi, P. (1985), "Enzymes Hosted in Reverse Micelles in Hydroarbon Solution," *Angew, Chem. Int. Ed. Engl.*, 24:439-450.

Laumen, L., et al. (1985), "Immobilized Porcine Liver Esterase: A Covenient Reagent for the Preparation of Chiral Building Blocks," *Tetrahedron Lett.*, 26(4):407-410.

Tor, Y., et al. (1989), "Enzyme Stabilization by Bilayer 'Encagement'," *Enzyme Microb. Technol.*, 11:306-312.

Wong, C. H. (1989), "Enzymatic Catalysts in Organic Synthesis," *Science*, 244:1145-1152.

*Primary Examiner*—David M. Naff
*Attorney, Agent, or Firm*—Arnold, White & Durkee

[57] ABSTRACT

Carrageenan-immobilized enzymes are prepared that are stable and retain high activity toward substrates when used in substantially water-immiscible organic solvents. The carrageenan-immobilized enzymes are preferably prepared by introducing droplets of an enzyme/carrageenan solution into a chilled alcohol saturated with a potassium salt and hardening the droplets in the alcohol. The alcohol is selected from n-butanol, benzyl alcohol, crotyl alcohol, n-propanol, isopropanol and sec-butanol. Reactions catalyzed by a κ-carrageenan-immobilized esterase include steroselective transesterifications and hydrolysis reactions.

13 Claims, 1 Drawing Sheet

CARRAGEEMAN-IMMOBILIZED ESTERASE

The U.S. Government may have certain rights in the invention pursuant to the terms of Grant No. GM 36786 awarded by the National Institutes of Health as a Small Business Innovation Research Grant.

BACKGROUND OF THE INVENTION

1. Field of the Invention

The invention relates generally to immobilization of enzymes in a carrageenan matrix. In particular aspects, carrageenan immobilized enzymes effectively catalyze reactions in organic solvents. Typical reactions include stereoselective transesterification and hydrolysis reactions.

The following is a table of abbreviations used.

TABLE 1

| | |
|---|---|
| ee | enantiomeric excess |
| HPLC | High performance liquid chromatography |
| PLE | Pig liver esterase |
| MOPSO | 3-[N-morpholino]-2-hydroxypropanesulfonic acid |
| THF | tetrahydrofuran |
| ETOAc | ethyl acetate |
| MeOH | methyl alcohol |
| KOAc | potassium acetate |
| DMF | dimethyl formamide |
| HCl | hydrochloric acid |

2. Description of Related Art

Historically enzymes wee thought to function only in aqueous media; however it was shown by Klibanov (1985) and subsequently by others (Inaday et al, 1986; Luisi, 1985) that enzymes can and do function in organic solvents. This discovery has stimulated interest in developing enzyme systems that can be used to efficiently perform organic reactions, particularly reactions that are stereoselective and that without enzymes are difficult to perform. Enzymes have been used in aqueous systems to perform chemical reactions, for example, transesterifications and isomerizations. Some reactions have been achieved in organic solvents. There is increasing recognition of the value of enzymatic catalysis in organic solvents, especially since selectivity is often increased compared to the reaction in aqueous media. As noted in a review by Wong (1989), enzyme catalyzed dehydrations, transesterifications, aminolyses, and oxidoreductions in organic solvents are becoming more common.

However, there are drawbacks to using enzymes in organic solvents. In some cases a relatively large amount of enzyme is required, especially when powdered preparations are used. Vigorous stirring may also be required in order to assure adequate contact with the dissolved substrate. Enzyme preparations from powdered or freeze dried enzymes may suffer from lower activity and therefore function inefficiently. In some instances, enzymes may be inactivated in an organic solvent to the extent that catalyzed reactions, if they occur at all, are too slow to be useful.

Enzymes immobilized within various matrices have been widely used to catalyze reactions in aqueous systems (Schneider et al, 1985; Chibata et al, 1984); however, few have been developed for use in nonaqueous systems. In one of few examples, selected enzymes immobilized by gel entrapment in polyacrylamide cross linked with N,N'-methylenebisacrylamide yielded reverse micelles useful in water immiscible solvents such as isooctane (Fadnavis and Luisi, 1989). There has been some success in enhancing enzyme stability in water miscible organic solvents. In one method, a soluble enzyme was coated with polymeric glutaraldehyde and the layer then crosslinked with a second layer of polyacrylamide derivatives to create a synthetic cage around the enzyme (Tor et al, 1989).

A few processes have been developed using immobilized enzymes in organic solvents, often in membrane reactors. Essentially, an enzyme is imbedded in a matrix which is then exposed to a substrate dissolved in an appropriate solvent. A multiphase membrane reactor has been described (Matson, 1989) in which organic or aqueous soluble substrates may be transformed as they contact the membrane immobilized enzyme.

Despite the development of membrane reactors, there are drawbacks to using this method. The reactor design is usually elaborate and costly. A frequently encountered problem is membrane plugging which then interferes with mass transport.

There is, therefore, a need to develop methods of enzyme immobilization providing stable, efficient, easily handled enzymes, particularly immobilized forms which stabilize an enzyme in organic solvents. Such immobilized enzymes could catalyze numerous organic reactions capable of providing potentially large quantities of optically enriched materials useful either as intermediates or as products for industries producing pharmaceuticals, pesticides, and herbicides.

SUMMARY OF THE INVENTION

The present invention addresses one or more of the foregoing problems by providing an efficient method of performing organic transformations in organic solvents. Now it has been discovered that a hydrogel, carrageenan, may be adapted as an immobilization matrix for particular enzymes, allowing rapid and efficient stereoselective biocatalyzed transformations in organic solvents.

Overall and in general, the invention is a method of encapsulating enzymes in carrageenan in a hardened gel form. Such encapsulated enzymes retain surprisingly high activity in organic solvents and may be used to catalyze stereoselective reactions.

The method of enzyme immobilization comprises several steps. A carrageenan solution is prepared and mixed with an enzyme such as an esterase, and in preferred practice, with pig liver esterase. Generally κ-carrageenan is preferred for immobilization, but other carrageenans, for example, λ-carrageenans may be used, although these tend to be less soluble than κ-carrageenan. If heating is required to solubilize the carrageenan, the possibility of heat denaturation of the enzyme should be taken into account. Once the carrageenan and the enzyme are mixed, and before gelation has taken place, the solution may be formed into conveniently sized beads or particles. Alternatively, the solution may be allowed to gel spontaneously in the form of blocks or sheets. When beads are desired, small, generally round beads may be obtained by extruding the mixture from a needle tip and dropping into an immiscible solvent, usually an organic alcohol such as n-butanol, sec-butanol, crotyl alcohol, benzyl alcohol, isopropanol or n-propanol. If the immobilized enzyme is to be used in a hydrolysis reaction, secondary or tertiary alcohols, particularly sec-butanol, are preferred solvents in order to avoid transesterification reactions.

In the usual practice of the invention, a gel-encapsulated enzyme is hardened in an organic solvent containing an inorganic salt, preferably a potassium salt such as potassium nitrate, potassium fluoroborate or, more preferably, potassium acetate. Generally, when the carrageenan/enzyme mixture is dropped into organic solvent containing the selected salt, approximately round particles are formed. In the absence of a salt, gel-particles are not well-formed, are soft and may be difficult to handle. Gel-encapsulated enzymes generally do not perform well as catalysts in organic syntheses, as compared to enzymes in a salt-hardened carrageenan matrix.

The inventors have discovered that forming and hardening of carrageenan encapsulated enzymes in an organic solvent containing an inorganic salt provides an immobilized enzyme that is stable and surprisingly active in organic solvents. The hardening period in the solvent may be relatively short, usually about 5 min, but longer times may be used if convenient. The particles may then be conveniently filtered using a Buchner funnel, sintered glass or the like. If not used immediately, gel-encapsulated enzyme preparations may be stored at 4° C.

In one aspect of the invention, carrageenan encapsulated enzyme, for example, pig liver esterase, may be used to convert organic substrates to chiral products. The starting materials may be chiral or achiral, for example, the dimethyl ester of 3-methyl glutaric acid, the 3-phenyl substituted dimethyl ester of glutaric acid, dimethyl 1,2 cyclohexenyl dicarboxylate, dimethyl 3-phenyl glutarate, dimethyl 1,2 cyclohexane dicarboxylate or similar compounds. A reaction mixture is prepared which contains an organic substrate and a carrageenan encapsulated enzyme in an organic solvent, preferably methyl t-butyl ether, hexane, n-butanol, ethyl ether or benzyl alcohol. The solvent selected will depend on the starting material and the type of reaction. The mixture is then incubated, preferably at 38° C. for a period of time sufficient to allow formation of a chiral product. The product may then be isolated from the reaction mixture by any one of numerous well-known methods, for example HPLC, gas chromatography or by chemical separation of diastereoisomeric derivatives.

Reactions have been run at 38° C. but as is recognized by those of skill in the art, higher reaction temperatures generally induce faster reactions. Although the use of higher temperatures is contemplated in the practice of the invention, the stability of the encapsulated enzyme to heat must be taken into account, as well as the temperature limitations of the solvent.

Yet another aspect of the invention is a composition comprising carrageenan encapsulated enzyme wherein the enzyme retains biocatalytic activity after immobilization, particularly in organic solvents. It may be that water retained in the carrageenan carrier contributes to maintaining enzyme activity, so that enzymes most amenable to carrageenan immobilization will be those requiring some amount of water to prevent conformational changes contributing to inactivation. In any event, esterases appear to be quite amenable to carrageenan immobilization with carrageenan-immobilized pig liver esterase being a particularly preferred composition.

DETAILED DESCRIPTION OF PREFERRED EMBODIMENTS

Figure 1:
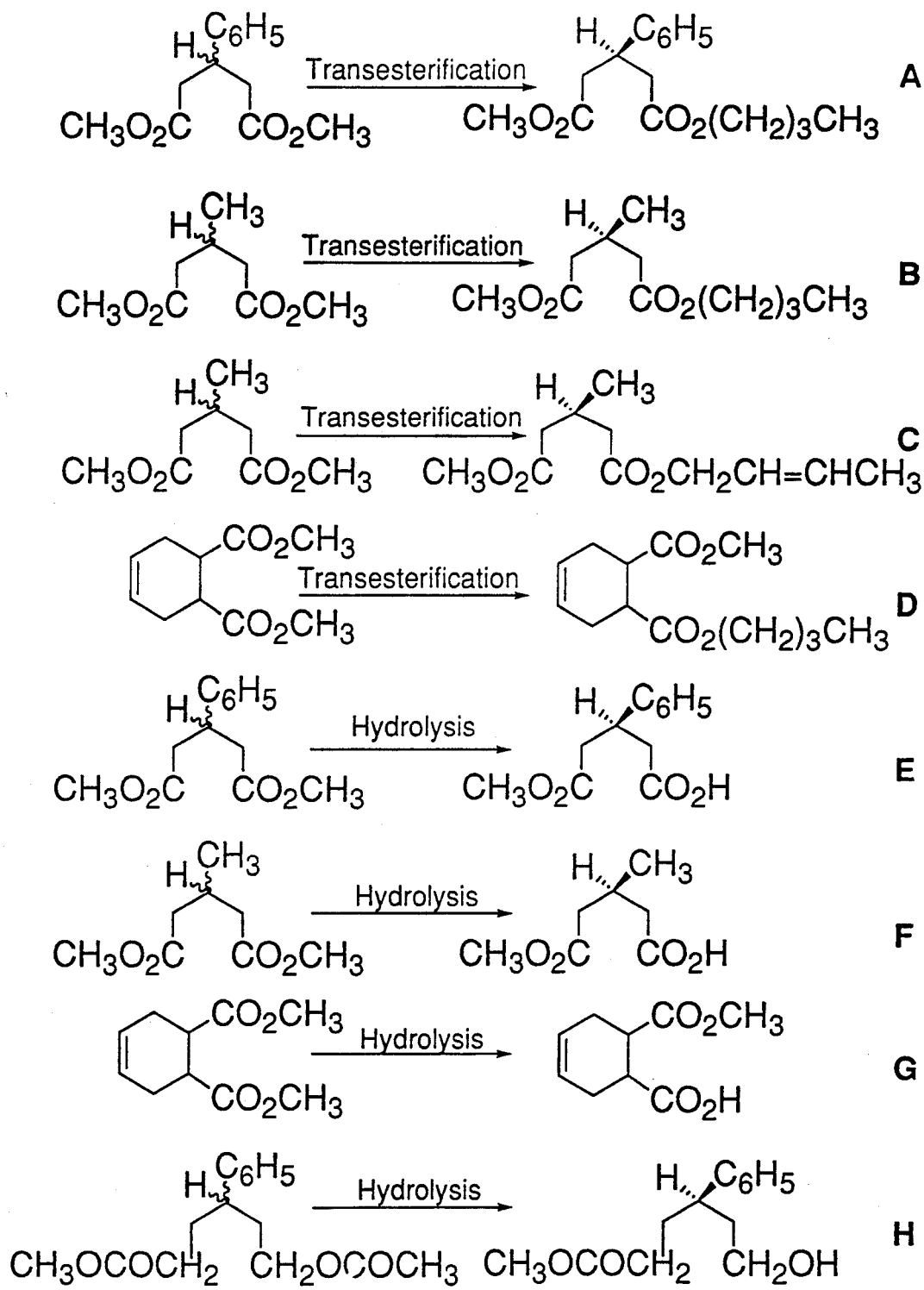
FIG. 1 shows the structures of the compounds used as substrates in examples 2-7 for carrageenan immobilized PLE esterifications and hydrolysis reactions.

The invention generally relates to a method of immobilizing enzymes in a carrageenan matrix. The method provides immobilized enzymes that are stable and retain virtually full biocatalytic activity in organic synthetic reactions in organic solvents. Carrageenan immobilized enzymes are particularly useful in performing stereoselective transformations, such as hydrolysis and transesterification reactions.

Examples of hydrolysis reactions catalyzed by carrageenan immobilized PLE are shown in Table 2.

TABLE 2

| Substrate | Product | Yield (%) | Time (hr) | % EE |
|---|---|---|---|---|
| DMPG | BPGA | 80 | 40 | 86 |
| DMMG | BMGA | 85 | 72 | 44 |
| CDC | CMCC | 90 | 24 | >95 |

DMPG: Dimethyl-(3-phenyl)-glutarate
DMMG: Dimethyl-(3-methyl) glutarate
CDC: Dimethyl ester of cyclohexene 1,2-dicarboxylic acid
BPGA: N-butyl, methyl-(3-phenyl) glutarate
BMGA: N-butyl, methyl-(3-methyl) glutarate
CMCC: 4-carbomethyoxy-5-carbonbutoxy-cyclohexene The present invention immobilizes enzymes in a natural polysaccharide isolated from seaweed. The polysaccharide is a high molecular weight material composed of galactose units joined by $\beta$,4-alpha glycosidic linkages. Known as carrageenan, the polymer is partially sulfonated and is commonly obtained as a sodium/potassium sulfate salt. The negative charge on the polymer may stabilize proteins which are entrapped within the polymer matrix during immobilization. Carrageenan has been used to stabilize proteins in solution and to immobilize whole cells, for example, microorganisms. A few instances of enzyme immobilization have been reported, but use was limited to aqueous solutions. A major disadvantage of aqueous applications is relatively extensive leakage of the enzyme from the carrageenan matrix.

Although single enzyme immobilization has been demonstrated, multiple enzyme immobilization should be feasible on similar principles. It should, for example, be possible to create layers of concentrically immobilized enzymes. Thus a substrate could diffuse into the immobilization matrix and be subjected in series to an appropriate catalytic sequence. The final product, if soluble in the organic solvent, should diffuse into the bulk solvent. On the other hand, if the final product were insoluble in the organic solvent, it would likely be trapped in the matrix. Unreacted soluble intermediates would diffuse from the matrix allowing the insoluble product t be readily isolated by filtration of the carrageenan particles. Additionally, cofactors required for enzyme action could also be entrapped within the carrageenan matrix, or, alternatively, covalently attached to one or more of the sugar hydroxyl groups.

Carrageenan-immobilized enzyme particles may be formed in a variety of ways. For example, an enzyme-carrageenan solution may be sprayed from an aerosol into a hardening solution (Lochmüller et al, 1987), sonicated in an immiscible solvent, or extruded from a vibrating needle into a water-immiscible solvent. These methods are well known in the art and may be used to vary the size of the immobilized enzyme particles. For example, formation of round particles ranging in size from 1 to several millimeters may be obtained by dropping a carrageenan-enzyme solution into a hardening solution from a syringe.

It has been discovered that hardening or curing of the carrageenan hydrogel in salt-containing alcohol provides a matrix that retains the enzyme while allowing it to display full biocatalytic activity. In particular, proper hardening may be used to provide particles that are readily handled, easily recovered and do not disintegrate during mixing with the substrate. Some hardening can be achieved with n-butanol alone, but the gel remains soft and encapsulated enzymes generally have low catalytic activity. By comparison, excellent catalytic activity is usually obtained when a potassium salt is dissolved in the alcohol used to harden the carrageenan gel matrix. Although, other potassium salts may be used, potassium acetate is most preferred. Solubility of the potassium salt appears to be a factor. Thus soluble potassium salts are most preferred hardening agents. Other salts might be used. Factors to consider are charge, interaction within the carrageenan matrix and the solubility of the salt in the organic solvent.

Transesterification or hydrolysis reactions catalyzed by immobilized PLE may be determined by the nature of the bulk solvent used. In primary alcohols such as n-butanol, transesterifications proceed efficiently while hydrolysis reactions are preferably run in secondary or tertiary alcohols such as sec-butanol, isopropanol or tert-butanol. In preferred practice, hydrolysis reactions are performed using enzymes encapsulated in carrageenan hardened in sec-butanol. This avoids transesterification when hydrolysis is the desired reaction.

It is understood that the invention is not limited to the carrageenan encapsulation of pig liver esterase. Other enzymes compatible with carrageenan hydrogel encapsulation may be prepared and used as biocatalysts in organic solvents, particularly esterases such as rabbit liver esterase, acetyl choline esterase, butyryl choline esterase, cholesterol esterase and other such similar enzymes with esterase activity. Carrageenan encapsulation is particularly useful for esterases and enzymes that may lose activity when used in powdered or freeze dried form. Lipase, for example, is not particularly active when used for transesterifications in organic solvents, requiring relatively large quantities of enzyme and long reaction periods. The effect of carrageenan immobilization on pig liver esterase is highlighted by comparing activity of the carrageenan immobilized enzyme with lyophilized preparations. Lyophilized pig liver esterase is virtually inactive in methyl tert-butyl ether in producing a chiral half-ester from a meso-diester. Carrageenan-encapsulated pig liver esterase provides a 71% yield of chiral product, demonstrating the protective effect of carrageenan matrix. Results are shown in example and Table 4.

The following examples of reactions catalyzed by PLE immobilized in carrageenan are intended only as illustrative. Table 3 summarizes some of these reactions which are not intended to be limiting. Structures of the substrates identified by letter in Table 3 and in the examples are shown in FIG. 1.

TABLE 3[a]

| Substrate | Time (hr) | Stereoselectivity (% ee) | Chemical Yield % |
|---|---|---|---|
| A | | 64 | 60 |
| B | | 26 | 95 |
| C | | 24 | 70 |
| D | 6[b] | 63 | 80 |
| E | | 82 | 75 |
| F | 8[b] | 90 | 60 |

[a]Reactions run at 38° C.
[b]Time represents period required for 50% yield.

Materials and Methods

Pig liver esterase (PLE) and yeast lipase (YL) were purchased from Sigma Chemical, St Louis, Mo. Respective activities were nominal activities of 200 units/mg and 30,000–100,000 units/mg protein. YL Sigma catalog number is L-9767.

Enzyme activity units, as measured for PLE are defined as one unit hydrolyzing 1.0 micromole of ethyl butyrate to butyric acid and ethanol per minute at Ph 8.0 at 25° C. Enzyme activity units for YL were determined at pH 7.0 from incubation with olive oil.

Carrageenan was obtained from Sanofi Corporation, a division of Elf Agitaine.

All reactions were run at 38° C. unless otherwise specified.

EXAMPLE 1

Carrageenan Immobilized Pig Liver Esterase 8 ml of deionized water and 250 mg of sodium κ-carrageenan were stirred at 40° C. until all solids had dissolved. A solution of 12.5 mg of pig liver esterase (PLE), approximate activity of 200 units per mg, in 2.5 ml of 0.1 M MOPSO buffer, pH 7.0, was added. The mixture was stirred and heated to 40° C. before extruding dropwise through an 18-gauge needle into 40 ml of ice-cold potassium acetate-saturated sec-butanol. After standing at 0° C. for 10 min, the solids were vacuum filtered on a Buchner funnel, washed twice with diethyl ether and used immediately or stored in an air-tight container at 4° C.

EXAMPLE 2

Transesterification

Preparation of 3-phenyl glutaric acid n-butyl methyl ester A

Immobilized pig liver esterase was prepared as described in Example 1. The immobilized enzyme was suspended in n-butanol and added to 15 ml of hexane containing 1 ml of n-butanol and 200 mg of 3-phenylglutaric acid dimethyl ester. The reaction was vigorously shaken on a wrist action shaker and the progress of the reaction monitored by gas chromatography (HP-1 crosslinked methyl silicone capillary column, 12 m×0.2 mm, 0.33 μm film thickness, oven temp. profile: 150° C. 1 min, 150° to 200° C. at 15° C./min, 200° C. for 3 min, FID detector, helium carrier at 15 ml min$_{-1}$, make-up at 40 ml min-1, hydrogen at 30 ml min-1, air at 22 ml min-$_1$, injection volume 2 μl). Elution times were as follows: dimethyl-3-phenyl glutarate (3.61 min), methyl-3-phenyl glutaric acid (4.08 min), butyl methyl-3-phenyl glutarate (5.60 min), and butyl-3-phenyl glutaric acid (6.33 min) and butyl-3-phenyl glutaric acid (6.33 min). After three days a 60% yield of the mixed butyl-methyl ester was obtained. Longer reaction times led to lower yields of the desired product due to formation of 3-phenylglutaric acid dibutyl ester as well as the half acids of methyl and butyl 3-phenylglutarate. The degree of stereoselectivity could not be ascertained by polarimetry due to low absolute rotations for this class of compounds (Heathcock et al, 1984).

Stereochemical information on the product was obtained by HPLC analysis of the alpha methyl benzyl amide diastereomers which were synthesized as follows: lithium iodide cleavage of the methyl ester moiety in refluxing pyridine (Hashimoto et al, 1986) followed by formation of the acid chloride using oxalyl chloride and DMF (Fujisawa and Toshio, 1987) and finally reaction of the acid chloride with R-(+)-alpha methyl benzyl amine to form the amide diastereomers. HPLC analysis using a 25 cm Alltech Econosil 5 m silica column, hexanemethyl acetate (60:40) as the eluant, and a flow rate of 1 ml/min revealed two peaks. The major component had a retention time of 7.54 min and the minor diastereomer eluted at 11.15 min. The diastereomeric ratio was 82:18 (64% ee).

EXAMPLE 3

Transesterification

Preparation of 3-methyl plutaric acid butyl methyl ester B

Carrageenan immobilized pig liver esterase prepared as described in Example i was added to a solution of 200 mg of 3-methyl dimethyl glutarate and 1 ml of n-butanol. The reaction progress was monitored by gas chromatography using the same conditions listed in Example 3. The elution order was: dimethyl ester, 1.1 min, monomethyl glutaric acid, 1.24 min; methyl-butyl diester, 2.17 min; monobutyl glutaric acid, 2.44 min; and finally the dibutyl diester, 3.81 min. After 1 day 95% of the meso diester had been converted to products. Selective cleavage of the methyl ester in the presence of the n-butyl ester followed by reaction with optically pure alpha methyl benzyl amine, as in Example 3, produced the amide-ester diastereomers. The diastereomers were separable by gas chromatography on a 12 m methylsilicone capillary column held at 190° C. for 5 min then ramped to 225° C. at a rate of 2° C./min then held at 225° C. for 5 min The minor component came off the column at 11.47 min and the major diastereomer eluted at 11.69 min. The ratio of diastereomers was 63:37 (26% ee).

EXAMPLE 4

Transesterification

Preparation of 3-methyl glutaric acid crotyl methyl ester C

Carrageenan immobilized pig liver esterase was prepared as described in Example 1 except that crotyl alcohol was used instead of n-butanol. The immobilized enzyme preparation was added to a mixture of 200 mg of 3-methyl glutaric acid dimethyl ester and 1 ml of crotyl alcohol. After 5 days the reaction reached a level of 70% conversion. The crotyl ester was hydrolyzed by warming the total isolated products with 2 ml of a 50:50 mixture of 3N HCl and THF. The reaction was extracted with ether and the ether then rinsed with 10 ml water followed by extraction of the organic phase with 10 ml of saturated sodium carbonate. The aqueous base layer was acidified with conc. HCl then extracted with ether. After drying over anhydrous MgSO4, the ether solution was filtered through cotton, and the solvent removed by rotary evaporation yielding 124 mg of oil. The material was subjected to the same diastereomer derivatization procedure as in Example 3 and separated by gas chromatography (12 m methylsilicone column, 175° C. to 225° C. at 5° C./min). The minor isomer eluted at 5.26 min followed by the major component at 5.35 min. The diastereomeric ratio was 62:38 (24% ee).

EXAMPLE 5

Transesterification

Preparation of Cyclohexane 3-butyl-4-methyl dicarboxylate D

Carrageenan immobilized pig liver esterase was prepared as described in Example 1 by forming and hardening the matrix in potassium acetate-saturated n-butanol. The immobilized enzyme preparation was added to 1ml of n-butanol containing 200 mg of cyclohexene 3,4-dimethyl carboxylate. The mixture was vigorously shaken for 2 days until 80% conversion as determined by HPLC. The stereoselectivity of the reaction was 63% ee as determined by HPLC of the amide diastereomers prepared from the product, cyclohexene 3-butyl-4-methyl dicarboxylate. The eluting solvent was 40% EtOAc in hexane at a flow rate of 1 ml/min. The minor diastereomer eluted from the column at 7.02 min followed by the major component at 7.34 min.

EXAMPLE 6

Hydrolysis

Preparation of methyl-3-phenylolutaric acid E

Carrageenan immobilized pig liver esterase prepared as described in Example 1 was added to 15 ml of MTBE containing 200 mg of 3-phenyl dimethyl glutarate. The mixture was shaken on a wrist action shaker at 40° C. and the reaction monitored by gas chromatography. After 75% conversion (2 days) the solution was filtered, beads washed with ether and the combined filtrate extracted with 20 ml of saturated sodium carbonate. The carbonate solution was acidified with conc. HCl and the product extracted into ether. The organic phase was rinsed with saturated NaCl, dried over MgSO4, filtered through cotton, and solvent removed to leave 163 mg of a thick clear oil. The acid was converted first to the acid chloride and then to a diastereomeric mixture of amides by the procedure described in Example 3. The isomers were separated by HPLC (38% EtOAc, 2% MeOH, 60% Hexane; flow rate 1.0 ml/min; 25 cm Alltech Econosil column) with the minor diastereomer eluting at 10.30 min followed by the major component at 14.30 min. The ratio Was 9:91 (82% ee).

EXAMPLE 7

Hydrolysis

Preparation of 3-carbomethoxy cyclohexane-4-carboxylic acid F

3-Carbomethoxy cyclohexene-4-carboxylic acid was prepared from 3-carbomethoxy cyclohexene-4-carboxylic acid methyl ester using the procedure described in Example 6. After 1 day the conversion was 60% and the stereoselectivity was greater than 90% ee as determined by the HPLC analysis of the amide diastereomers prepared as in Example 3. The HPLC eluting solvent was 40% EtOAc in hexane and the flow rate was 1 ml/min. The major isomer eluted at 10.9 min followed by the minor compound at 12.8 min.

EXAMPLE 8

Comparison of Activity of Carrageenan Immobilized PLE With Freeze Dried PLE

Three samples of PLE were compared for the ability to produce a chiral product in an organic solvent. PLE purchased from Sigma Chemical Co. was used as received. An aliquot was immobilized in carrageenan as described in Example 1. A second aliquot was freeze dried overnight in a lyophilizer (Labconco). A third sample of PLE was obtained as a freeze dried preparation purchased from Biocatalysts, Ltd (England). Two substrates were used to test each PLE preparation: 3,4-dicarbomethoxy cyclohexene (meso-CHDE) and the dimethyl ester of 3-methyl glutaric acid (meso-MDG). 2.5 mg of carrageenan immobilized PLE incubated with meso-cyclohexenyl dimethyl ester (meso-CHDE) in methyl tert-butyl ether for 24 hr produced 71% yield of product. The same reaction run with 5.0 mg enzyme as a freeze dried powder yielded 2.5% product. 100 mg of the commercial preparation yielded no product when run under the same conditions. Results are summarized in Table 4.

TABLE 4

| Enzyme | mg | % Chiral Product |
| --- | --- | --- |
| Immobilized PLE | 2.5 | 71[c], 83[d] |
| Lyophilized PLE[a] | 5.0 | 2.5[c], 0[d] |
| Lyophilized PLE[b] | 100 | 0[c], 0[d] |

[a]Prepared by lyophilization of purchased enzyme solution
[b]Purchased as a lyophilized preparation
[c]Substrate is meso-3,4-dimethyl cyclohexenyl carboxylate ester (meso-CHDE), product shown in FIG. 1, structure G
[d]Substrate is meso-dimethyl (3-methyl) glutaric acid ester (Meso-MDG), structure shown in FIG. 1, structure F

EXAMPLE 9

Hydrolysis

Yeast Lipase Catalyzed F and G

Yeast lipase from *Candida cylindracea* was immobilized in carrageenan as in Example 1 using 50 mg of lyophilized powder in 5 ml of MOPSO buffer. Hydrolysis products were obtained using two substrates, meso-3,4-dimethyl cyclohexenyl carboxylate (meso-CHDE) or the dimethyl ester of 3-methyl glutaric acid (meso-MDG). Reaction conditions were as in Example 8 with methyl tert-butyl ether as the solvent for the reaction. Table 5 shows respective products of the reaction, G and F as shown in FIG. 1. Yields leveled off at 70–80% after approximately 24–36 hours of reaction.

TABLE 5

Biocatalysis by Carrageenan Immobilized Yeast Lipase

| Substrate | Time (hr) | % Chiral Product |
| --- | --- | --- |
| meso-CHDE | 12 | 41 |
|  | 24 | 70 |
|  | 30 | 70 |
| meso-MDG | 5 | 16 |
|  | 24 | 61 |
|  | 36 | 78 |

Lyophilized yeast lipase powder was also used to convert meso-CHDE to chiral product. Yield using 50 mg of the powder was 84% after 20 hr.

The present invention has been described in terms of particular embodiments found by the inventors to comprise preferred modes of practice of the invention. It will be appreciated by those of skill in the art that in light of the present disclosure numerous modifications and changes can be made in the particular embodiments without departing from the intended scope of the invention. For example, many esterases other than pig liver esterase may be used and the reactions need not be limited to transesterification or hydrolysis but will be particular to the enzyme utilized, or under some conditions may be run as reverse reactions, e.g. esterification. All such modifications are intended to be included within the scope of the claims and not to affect the intended nature and practice of the invention.

PREFERENCES

The references listed below are incorporated herein by reference to the extent that they supplement, explain, provide a background for or teach methodology, techniques and/or compositions employed herein.

1. Chibata, I., Tosa, T. and Takata, I., U.S. Pat. No. 4,433,054, Feb. 21, 1984.
2. Fadnavis, N.W. and Luisi, P.L., Biotechnol. Bioeng. 33, 1277–1282 (1989)
3. Fujisawa, T. and Toshio, S., Org. Syn. 66, 121 (1987).
4. Hashimoto, S., Shinoda, T. and Ikegami, S., Tet. Lett. 27, 2885 (1986).
5. Heathcock, C., Rosen, T. and Watanabe, M., J. Org. Chem. 49, 3657–3659 (1984).
6. Inaday, Y., Takahashi, K., Yoshimoto, T., Ajima, A., Matsushima, A., and Saito, Y., Trends Biotechnol. 7, 190–194 (1986).
7. Klibanov, A.M., Zaks, A., Proc. Natl. Acad. Sci. USA 82, 3192–3196 (1985).
8. Lochmüller, C.H., Wigman, L.S. and Kitchell, B.S., J. Chem. Technol. and Biotechnology 40, 33–40 (1987).
9. Luisi, P.L., Angew. Chem. Int. Ed. 24, 439–450 (1985).
10. Matson, U.S. Pat. No. 4,800,162, Jan. 24, 1989.
11. Schneider, M., Reimerdes, E.H. and Laumen, K., Tet. Lettr. 26, 407–410 (1985).
12. Tor, R., Dror, Y. and Freeman, A. Enzyme Microb. Technol. 11, 306–312 (1989)
13. Wong, C.-H., Science 244, 1145–1152 (1989)

What is claimed is:

1. A method of preparing catalyticaly active carrageenan-immobilized esterase, comprising the steps:
   admixing an esterase with an aqueous carrageenan solution;
   introducing the esterase/carrageenan solution in the form of droplets into a chilled mixture of an alcohol selected from a group consisting of n-butanol, benzyl alcohol, crotyl alcohol, n-propanol, isopropanol and sec-butanol wherein the alcohol is saturated with a potassium salt that is substantially soluble in the alcohol;
   hardening the droplets in said alcohol to form the immobilized esterase in the form of a stable, matrix encapsulated sterase which is catalytically active in substantially water immiscible organic solvents.

2. The method of claim 1 wherein the carrageenan is a k-carrageenan.

3. The method of claim 1 wherein the carrageenan is pig liver esterase or lipase.

4. The method of claim 1 wherein the potassium salt is KCL, KNO₃, KOAc or KBF₄.

5. The method of claim 1 wherein the chilling is about 0° C.

6. The method of claim 1 wherein the introducing of droplets is by extrusion or aerosol spray.

7. The method of claim 1 wherein the carrageenan-immobilized esterase is used or catalytic conversion of an organic substrate to a chiral product by admixing an organic substrate and the carrageenan-immobilized esterase in a substantially water immiscible organic solvent; and maintaining contact between the organic substrate and said esterase for a period of time sufficient for a chiral product to form.

8. The method or claim 7 wherein the organic substrate is chiral or achiral.

9. The method of claim 7 wherein the esterase is pig liver esterase.

10. The method of claim 7 wherein the substantially water immiscible organic solvent is n-butanol, methyl t-tubyl ether, ethyl ether, benzyl alcohol or hexane.

11. The method of claim 7 wherein the catalystic conversion is transesterification or ester hydrolysis.

12. The method of claim 7 wherein the organic substrate is dimethyl ester of 3-methyl glutyaric acid, 3-phenyl substituted dimethyl ester of glutaric acid, dimethyl ester of glutaric acid, dimethyl 1,2-cyclohexenyl dicarboxylate, dimethyl 3-phenyl glutaerate or dimethyl 1,2-cyclohexane carboxylate.

13. A carrageenan-immobilized sterase produced by the method of claim 1 wherein the esteroial is pig liver esterase.

* * * * *

UNITED STATES PATENT AND TRADEMARK OFFICE
CERTIFICATE OF CORRECTION

PATENT NO. : 5,262,313
DATED : November 16, 1993
INVENTOR(S) : Barbars S. Kitchell, et al It is certified that error appears in the above-indentified patent and that said Letters Patent is hereby corrected as shown below:

```
on the title page, Item [54]: "CARRAGEMAN-" should read --CARRAGEENAN--.
Column 1, line 2, "CARRAGEEMAN-" should read --CARRAGENAN--.
Column 10, line 57:    Change the word "sterase" to esterase
Column 10, line 64:    Change the term "KCL" to KCl
Column 11, line 2:     Change the word "or" to for
Column 12, line 3:     Change the word "t-tubyl" to butyl
Column 12, line 4:     Change the word "catalystic" to catalytic
Column 12, line 7:     Change the word "glutyaric" to glutaric
Column 12, line 10:    Change the word "glutaerate" to glutarate
Column 12, line 12:    Change the word "sterase" to esterase
Column 12, line 13:    Change the word "esteroial" to esterase
```

Signed and Sealed this

Thirty-first Day of May, 1994

*Attest:*

BRUCE LEHMAN

*Attesting Officer*     Commissioner of Patents and Trademarks